(12) United States Patent
Steadman Booker et al.

(10) Patent No.: US 10,557,806 B2
(45) Date of Patent: Feb. 11, 2020

(54) CT SYSTEM AND CT METHOD

(71) Applicant: KONINKLIJKE PHILIPS N.V., Eindhoven (NL)

(72) Inventors: Roger Steadman Booker, Aachen (DE); Ewald Roessl, Ellarau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 101 days.

(21) Appl. No.: 15/765,726

(22) PCT Filed: Oct. 12, 2016

(86) PCT No.: PCT/EP2016/074443
§ 371 (c)(1),
(2) Date: Apr. 4, 2018

(87) PCT Pub. No.: WO2017/071952
PCT Pub. Date: May 4, 2017

(65) Prior Publication Data
US 2018/0284035 A1 Oct. 4, 2018

(30) Foreign Application Priority Data
Oct. 28, 2015 (EP) .................................... 15191824

(51) Int. Cl.
G01N 23/04 (2018.01)
G01N 23/046 (2018.01)
A61B 6/00 (2006.01)
A61B 6/03 (2006.01)

(52) U.S. Cl.
CPC .......... *G01N 23/046* (2013.01); *A61B 6/032* (2013.01); *A61B 6/4014* (2013.01); *A61B 6/5282* (2013.01)

(58) Field of Classification Search
CPC .... G01N 23/046; A61B 6/032; A61B 6/4014; A61B 6/5282; G01T 1/2985
USPC .............................................................. 378/4
See application file for complete search history.

(56) References Cited

U.S. PATENT DOCUMENTS

| 7,680,241 B2 | 3/2010 | David |
| 2004/0114710 A1 | 6/2004 | Ozaki |
| 2011/0311019 A1 | 12/2011 | Ribbing |
| 2013/0259344 A1 | 10/2013 | Petersilka |

FOREIGN PATENT DOCUMENTS

WO 2007/149749 12/2007

*Primary Examiner* — David P Porta
*Assistant Examiner* — Gisselle M Gutierrez
(74) *Attorney, Agent, or Firm* — Larry Liberchuk

(57) ABSTRACT

The present invention relates to a dual- or multi-source CT system and method. For suppressing or even completely eliminating the negative effects of cross-scatter, the proposed CT system comprises two x-ray sources (10, 11), two detectors (13, 14), two read-out units (15, 16), a control unit (17) and a reconstruction unit (19). Further, a scatter correction unit (18) is provided or the read-out units (15, 16) are configured to generate scatter-corrected read-out signals from the detected radiation, wherein a scatter-corrected read-out signal is generated from the radiation detected by a detector during a single projection interval (I) including multiple repetitions of three phases, in which the sources are alternately switched on and off and in which the read-out units alternately register primary radiation or cross-scatter radiation.

14 Claims, 5 Drawing Sheets

CT SYSTEM AND CT METHOD

CROSS REFERENCE TO RELATED APPLICATIONS

This application is the U.S. National Phase application under 35 U.S.C. § 371 of International Application No. PCT/EP2016/074443, filed Oct. 12, 2016, published as WO 2017/071952 on May 4, 2017, which claims the benefit of European Patent Application Number 15191824.0 filed Oct. 28, 2015. These applications are hereby incorporated by reference herein.

FIELD OF THE INVENTION

The present invention relates to a CT system and a corresponding CT method.

BACKGROUND OF THE INVENTION

In Computed Tomography (CT) measures are in place to avoid that scatter photons impinge on the detector. To this end, so called anti-scatter grids have evolved to offer scatter attenuation on both angular (phi) and longitudinal (z) directions. However, despite such measures, sophisticated Monte Carlo based software corrections are required in order to completely eliminate the remaining artifacts caused by scatter events. This is particularly difficult in dual source systems, where sources influence each other's corresponding detectors with cross-scatter, i.e. photons from one source may impinge on the wrong detector due to scattering through the patient or object. Further, such anti-scatter corrections to some extent require a large degree of computation effort.

US 2004/114710 A1 discloses an X-ray CT apparatus including a plurality of X-ray irradiation sources and a plurality of X-ray detection units. Timing of irradiation of X-ray is shifted by each X-ray irradiation source, the detection unit separately obtains projection data and scatter correction data. In a scatter correction unit, scatter correction is performed based on the projection data and the scatter correction data.

US 2011/311019 A1 discloses a tomographic apparatus including at least two x-ray sources that are concurrently driven with different switching patterns to generate uniquely encoded radiation. The tomographic apparatus further includes at least two detectors that each detect primary radiation emitted by its corresponding one of the at least two x-ray sources and cross scatter radiation from at least one of the other at least two x-ray sources. Each of the at least two detectors produces an aggregate signal representative of the detected primary and cross scatter radiation. The tomographic apparatus further includes a decoupler which, based on the different switching patterns, identifies at least one signal corresponding to at least one of the at least two x-ray sources within the aggregate signal and associates the identified signal with its corresponding x-ray source.

SUMMARY OF THE INVENTION

It is an object of the present invention to provide an alternative and improved CT system and CT method with two x-ray sources for suppressing or even completely eliminating the negative effects of cross-scatter.

In a first aspect of the present invention a CT system is presented comprising two x-ray sources for rotating about and concurrently or subsequently emitting radiation through an imaging region, two detectors, one per x-ray source, for detecting radiation after penetration through the imaging region, two read-out units, one per detector, for reading out the detected radiation from the respective detector, a control unit for controlling said x-ray sources by alternately switching each of said x-ray sources on and off so that in a first phase only the first x-ray source emits radiation, in a second phase both x-ray sources emit radiation and in a third phase only the second x-ray source emits radiation and for controlling said read-out units such that radiation detected by a detector during a phase in which the corresponding x-ray source is switched off is distinguished from radiation detected by the same detector during a phase in which the corresponding x-ray source is switched on, and a reconstruction unit for reconstructing a projection from scatter-corrected readout-signals, wherein a scatter correction unit is provided or the read-out units are configured to generate scatter-corrected read-out signals from the detected radiation, wherein a scatter-corrected read-out signal is generated from the radiation detected by a detector during a single projection interval including multiple repetitions of said three phases and read out by the corresponding read-out unit.

In a further aspect of the present invention a CT method is presented using a CT system comprising two x-ray sources for rotating about and concurrently or subsequently emitting radiation through an imaging region, two detectors, one per x-ray source, for detecting radiation after penetration through the imaging region, and two read-out units, one per detector, for reading out the detected radiation from the respective detector, said CT method comprising controlling said x-ray sources by alternately switching each of said x-ray sources on and off so that in a first phase only the first x-ray source emits radiation, in a second phase both x-ray sources emit radiation and in a third phase only the second x-ray source emits radiation, controlling said read-out units such that radiation detected by a detector during a phase in which the corresponding x-ray source is switched off is distinguished from radiation detected by the same detector during a phase in which the corresponding x-ray source is switched on, generating scatter-corrected read-out signals from the detected radiation, wherein a scatter-corrected read-out signal is generated from the radiation detected by a detector over multiple repetitions of said three phases and read out by the corresponding read-out unit, and reconstructing an image from the scatter-corrected read-out-signals.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed system, in particular as defined in the dependent claims and as disclosed herein.

The present invention is based on the idea to actively measure the cross-scatter. In particular, the acquisition of data indicative of the amount (and, optionally, spectral footprint) of cross-scattered photons originating from one or more x-ray source(s) other that the one corresponding to the detector is proposed. This additional information is used to seed or fine-tune the correctional measures to avoid imaging artifacts caused by cross-scatter. For this purpose, the fast-switching capability of x-ray sources is exploited to divide the acquisition time into sub-intervals (phases), in which either primary radiation or cross-scatter radiation is measured independently. This, in turn, provides the possibility to gather cross-scatter information on a projection-by-projection basis.

Further, the scatter-corrected read-out signals are generated from the radiation detected by the corresponding detector over multiple repetitions of said three phases, which multiple repetitions are all part of a single projection interval. This provides a more flexible and advantageous approach compared to the apparatus and method disclosed in US 2004/114710 A1, according to which the primary transmission data for any detector is sampled irregularly in the angular coordinate. According to US 2004/114710 A1 the scatter and data readings are not interleaved during one projection interval (also called acquisition interval or frame), and the various scatter components are acquired one after the other once during each projection interval. In contrast, according to the present invention the scatter and data readings are repeated multiple times during one projection interval, and from all these data (acquired during one projection interval) a scatter-corrected read-out signal is generated, which is then used for image reconstruction and for generating a projection. Thus, for each angular position a separate projection is generated from radiation detected during a single projection interval corresponding to said angular position, wherein a projection interval is sub-divided into sub-intervals in which the x-ray sources are multiple times switched on and off according to the above described switching pattern.

Hence, according to the present invention the sub-sampling pattern is repetitive within each frame and much more flexible. This makes the sensing of scatter and cross-scatter more homogenous compared to the known solution, i.e. the obtained data including the cross-scatter data is sampled homogenously in time (and hence angle) within each projection interval.

In a preferred embodiment the read-out units are configured to take the time length of said three different phases into account in the generation of the scatter-corrected read-out signals. This further improves the accuracy of the scatter correction, particularly if the time lengths of the different phases are different.

Preferably, each read-out unit comprises a counter configured to increment its count based on radiation detected by the corresponding detector during phases in which the corresponding x-ray source is switched on and to decrement its count based on radiation detected by the corresponding detector during phases in which the corresponding x-ray source is switched off. A counter is particularly useful in the exact measurement of the detected radiation in the different phases. Further, a counter (also called counting electronics) allowing to re-direct the acquired impinging photons depending on the phase of the switching pattern (i.e. the switching of x-ray sources in the different phases). Thus, the information is separated as it impinges the detector.

The counters are preferably configured to decrement its count based on radiation detected by the corresponding detector during phases in which the corresponding x-ray source is switched off multiplied by a correction factor corresponding to the ratio of the time length of the phases in which the corresponding x-ray source is switched on to the time length of the phases in which the corresponding x-ray source is switched off. This embodiment takes the time lengths of the different phases into account.

In another embodiment each read-out unit comprising a scatter counter and a radiation counter, wherein the control unit is configured to control the read-out units such that radiation detected by a detector during a phase in which the corresponding x-ray source is switched off is read out by the scatter counter of the corresponding read-out unit to obtain a scatter signal and that radiation detected by the same detector during a phase in which the corresponding x-ray source is switched on is read out by the radiation counter of the same read-out unit to obtain a radiation signal, and wherein the read-out units are further configured to correct scatter by subtracting the scatter signal from the radiation signal read out by the scatter counter and the radiation counter of the same read-out unit to obtain the scatter-corrected read-out signals. This provides a simple and reliable implementation. Preferably, in this embodiment the ratio of the respective sampling durations in the various phases, i.e. the time length of said three different phases, is taken into account in the generation of the scatter-corrected read-out signals.

Each read-out unit may further comprise a switch controlled by the control unit to switch the detected radiation to scatter counter or the radiation counter in the respective phases or an enabling logic controlled by the control unit to enable or disable the scatter counter or the radiation counter in the respective phases.

Further, in order to obtain spectral information as well, each read-out unit may further comprise two or more radiation counters and/or two or more scatter counters for energy-dispersive counting.

In another embodiment the control unit is configured to control said read-out units such that radiation detected by a detector during the three different phases is distinguished and that a scatter-corrected read-out signal is generated by the read-out unit corresponding to said detector from the detected radiation in the three different phases. According to this embodiment, the timing of the x-ray source is the same as explained above, but the grouping of the different phases within a projection interval at the detector is different. In this case, during the overlap phase (during which both x-ray sources are switched on) a detector acquires radiation data (based on radiation from the assigned x-ray source) plus scatter data (resulting from radiation from the respective other x-ray source). Those two readings can be corrected by the scatter intensity estimated from the adjacent (in-time) measured scatter intensity signals acquired in the other two phases (in which one of the x-ray sources is respectively switched off) and the known ratio of the durations of the three phases.

In an alternative embodiment the read-out unit does not comprise counters but each read-out unit comprises an integrator configured to provide an integration value after each phase, which are used for generating said scatter-corrected read-out signals.

The generation of the scatter-corrected signals may be performed by the read-out units, which may be adapted accordingly. Alternatively, separate means may be provided, in particular as part of the read-out units.

In a further embodiment the control unit is configured to control said scatter correction unit or said read-out units such that subsequent scatter-corrected read-out signals are each generated from the radiation detected by a detector during subsequent projection intervals each having the same duration. This provides that the different projections are comparable.

In still another embodiment the control unit is configured to control said x-ray sources to alternately switch each of said x-ray sources on and off according to the same switching pattern during subsequent projection intervals. This further ensures the homogeneous sensing of the radiation in the sense that every single projection is acquired with the same switching pattern and that the different projections are comparable. The information of primary radiation, scatter and primary radiation plus scatter is attained within each projection, whereas according to US 2004/114710 A1 and US 2011/311019 A1 such a switching pattern or "aggregate" can only be obtained on basis of different projections, i.e. every projection hast a distinct aggregate signal but it remains the same within a projection.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
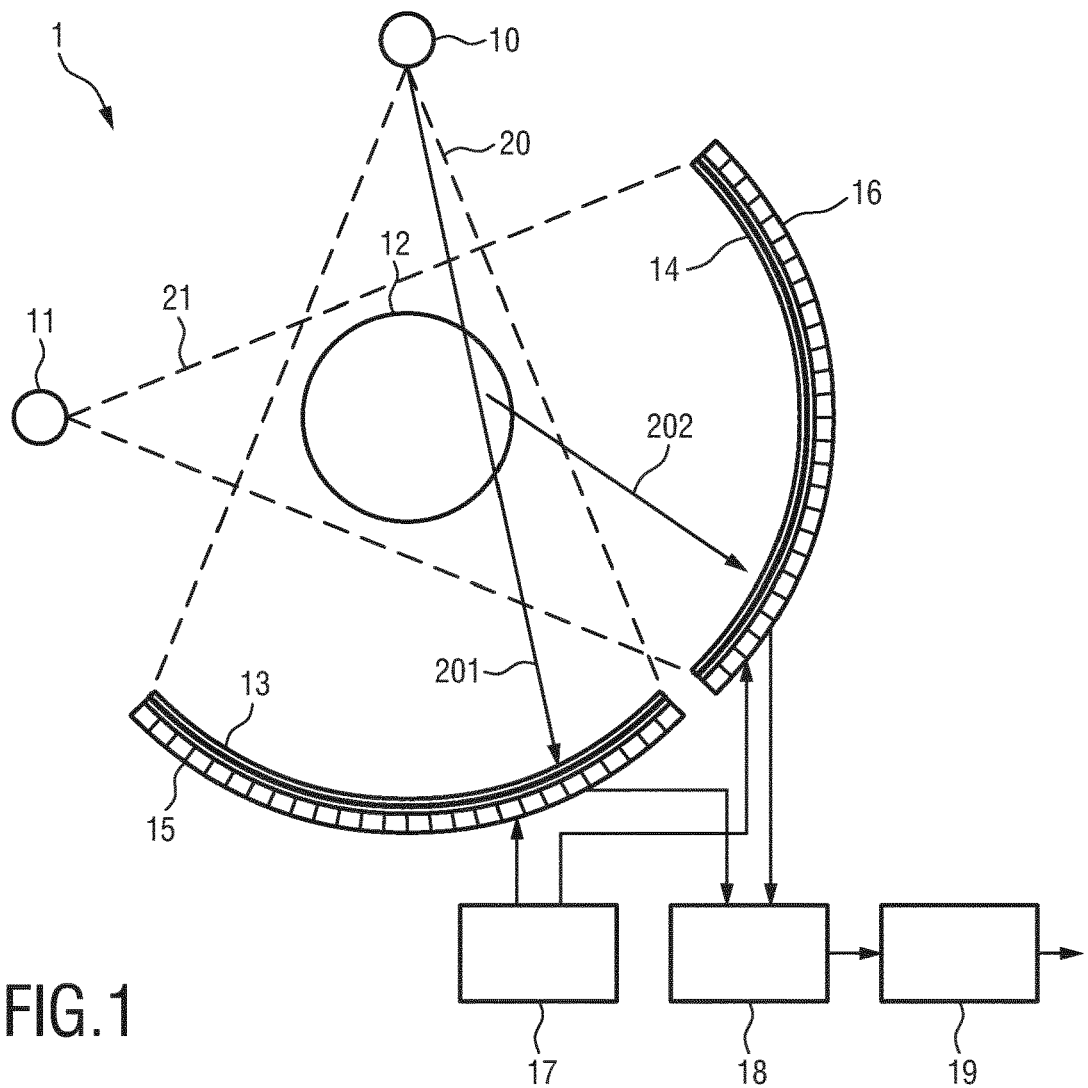
FIG. 1 shows a schematic diagram of a first embodiment of a CT system according to the present invention.

FIG. 1 shows a schematic diagram of a first embodiment of a CT system 1 according to the present invention. It comprises two x-ray sources 10, 11, which are in this example displaced by a rotational angle of about 90°, for rotating about and concurrently or subsequently emitting radiation 20, 21 through an imaging region 12, in which an object of examination is arranged, e.g. a patient on a patient table. Two detectors 13, 14, one per x-ray source 10, 11, are arranged opposite the respective x-ray source 10, 11, for detecting radiation after penetration through the imaging region 12. Two read-out units 15, 16, one per detector 13, 14, are provided for reading out (preferably per pixel or groups of pixels) the detected radiation from the respective detector 13, 14. Further, a control unit 17 is provided for controlling said x-ray sources 10, 11 and said read-out units 15, 16. An optional scatter correction unit 18 generates scatter-corrected read-out signals from the detected radiation. Alternatively, the generation of the scatter-corrected read-out signals may also be performed by the read-out units 15, 16, which may be configured accordingly in some embodiment, i.e. the function of scatter correction may be performed inherently by the read-out units or by separate means. A reconstruction unit 19 reconstructs an image from the scatter-corrected readout-signals, i.e. a projection is generated per projection interval.

It shall be noted that the proposed CT system may comprise more than two x-ray sources, detectors and read-out units, in which case the proposed operation described in the following may be applied in the same manner with a corresponding adaptation to the respective number of x-ray sources, detectors and read-out units. The read-out units are preferably integrated with the respective detector into a detection unit, which may generally be a counting or integrating detection unit, as will also be explained in more detail below.

According to the present invention, an acquisition sequence is proposed allowing measuring both primary radiation (photons) and cross-scatter radiation. In particular, detector 13 is configured to measure in an interleaved manner primary radiation originating from source 10 and cross-scatter photons which were originated from source 11. In the same manner detector 14 is configured to measure in an interleaved manner primary radiation originating from source 11 and cross-scatter photons which were originated from source 10. Due to the availability of fast grid switching in x-ray sources, sub-µs transient times are possible, allowing having multiple on/off phases (i.e. different switching modes) of the x-ray source within one acquisition interval or projection.

Hence, according to the present invention the control unit 17 is configured to control said x-ray sources by alternately switching each of said x-ray sources 10, 11 on and off so that in a first phase only the first x-ray source 10 emits radiation, in a second phase both x-ray sources 10, 11 emit radiation and in a third phase only the second x-ray source 11 emits radiation. Further, the control unit controls said read-out units 15, 16 such that radiation detected by a detector during a phase in which the corresponding x-ray source is switched off is distinguished from radiation detected by the same detector during a phase in which the corresponding x-ray source is switched on.

The scatter correction unit 18 generates scatter-corrected read-out signals from the detected radiation, wherein a scatter-corrected read-out signal is generated from the radiation detected by a detector over multiple repetitions of said three phases and read out by the corresponding read-out unit, i.e. from the radiation acquired during the different phases of a switching pattern run through during a single projection interval. Alternatively, depending on the particular implementation, the read-out units 15, 16 may be configured to generate the scatter-corrected read-out signals in this way.

Figure 2:
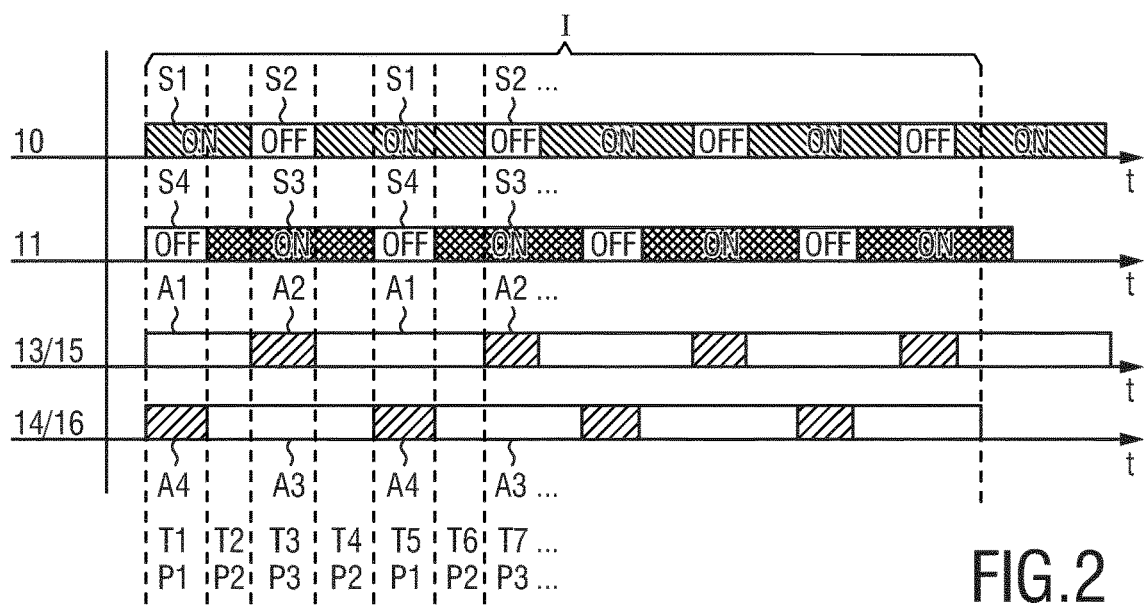
FIG. 2 shows a timing diagram illustrating a first implementation of the data acquisition.

This operation is illustrated in FIG. 2 which shows a basic timing diagram indicating the sequence of active/inactive phases (i.e. different switching modes) of both sources 10, 11 and the acquisition of the corresponding radiation. In this embodiment, two distinct acquisition modes A1, A2 and A3, A4 of each of the read-out units 15, 16 are considered, while two switching modes S1, S2 and S3, S4 of each of the x-ray sources 10, 11 can be distinguished. From the combination of these different acquisition phases and switching modes three different types of overall phases can be distinguished that are repeated over time.

In a first time interval T1, representing a first phase P1, the first source 10 is on (switching mode S1) and the second source 11 is off (switching mode S4). The radiation is detected by both detectors 13, 14, wherein the radiation detected by the first detector 13 is registered by the corresponding read-out unit 15 as primary radiation 201 (acquisition mode A1) and the radiation detected by the second detector 14 is registered by the corresponding read-out unit 16 as cross-scatter radiation 202 (acquisition mode A4), in which the cross-scatter photons of the opposite source 10 are registered.

In a second time interval T2, representing a second phase P2, both sources 10, 11 are on (switching mode S1 for source 10 and switching mode S3 for source 11). The radiation is detected by both detectors 13, 14, wherein the radiation detected by the first detector 13 is registered by the corresponding read-out unit 15 as primary+cross-scatter radiation (acquisition mode A1) and the radiation detected by the second detector 14 is registered by the corresponding read-out unit 16 as primary+cross-scatter radiation (acquisition mode A3).

In a third time interval T3, representing a third phase P3, the first source 10 is off (switching mode S2) and the second source 11 is on (switching mode S3). The radiation is detected by both detectors 13, 14, wherein the radiation detected by the first detector 13 is registered by the corresponding read-out unit 15 as cross-scatter radiation (acquisition mode A2) and the radiation detected by the second detector 14 is registered by the corresponding read-out unit 16 as primary radiation (acquisition mode A3).

In a fourth time interval T4 the settings and operations are the same as in the second time interval, i.e. the fourth time intervals also represents a second phase P2. Thereafter, the phases P1-P2-P3-P2 are repeated multiple times, in this example four times, over the acquisition interval I.

Hence, the cross-scatter radiation registered in phases P1 and P3 by the different read-out units 15, 16 over the whole acquisition interval I, over which the different phases P1 to P3 are homogenously distributed, can be used to estimate the amount of scatter that affected the acquisition in phases P2, which estimate can then be used to assist the (offline) scatter correction. In the example shown in FIG. 2 consecutive frames (denoted by I) are identical and the time structure within a frame I is much less critical to reconstruct as changes from frame to frame. Hence, as mentioned above, the different phases P1 to P3 are homogenously distributed, which refers to the distribution from one frame to the next frame. Sub-frames can have any length as long as consecutive frames (e.g. frame I and frame I+1) are comparable.

In case of using fast switching x-ray tubes as x-ray sources 10, 11, a signal that indicates the status of the respective x-ray source is readily available. A clear distinction of the different acquisition modes A1 and A2 (for the first read-out unit 15) and A3 and A4 (for the second read-out unit 16) in phases P1 and P3 can thus be made. The control of the read-out units 15, 16, i.e. to set them into the correct acquisition mode, can simply be effected by switching them into the correct acquisition mode by use of the switching signals used for switching the corresponding source 10, 11 into the correct switching mode (i.e. to switch it on or off) or by use of another switching status signal indicating the switching mode of the corresponding source 10, 11.

Figure 3:
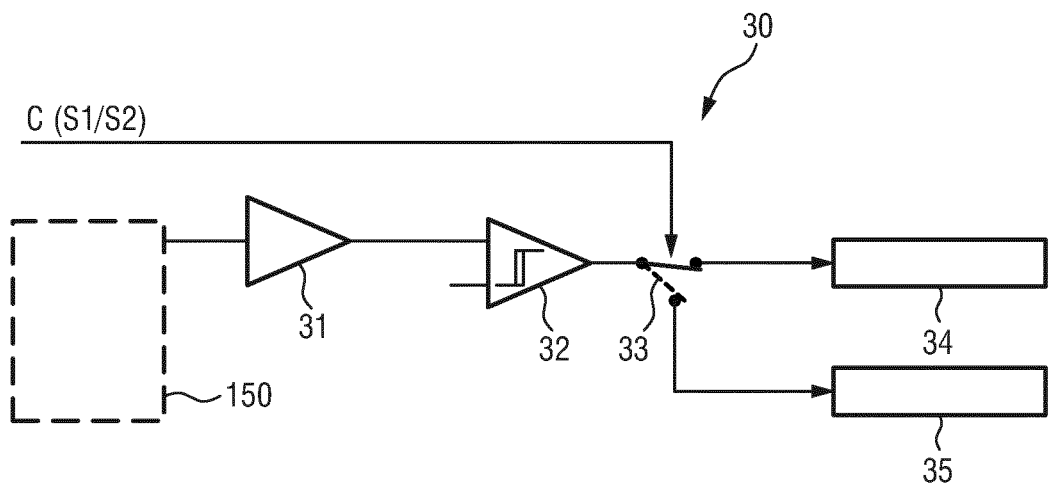
FIG. 3 shows a circuit diagram of a first embodiment of a read-out unit according to the present invention.

FIG. 3 shows a circuit diagram of a first embodiment of a read-out unit 30 according to the present invention, wherein the circuitry of the read-out unit for reading out one detector element 150 (or a group of detector elements; in this example of the first detector 15 which is preferably a direct conversion detector) is shown. The read-out unit 30 comprises a CSA (Charge Sensitive Amplifier)+pulse shaping unit 31 coupled to the detector element 15, a discriminator (also called threshold unit) 32, a switching unit 33, a radiation counter 34 and a scatter counter 35. Based on the switching mode of the respective source (in this example the first source 10), providing a signal indicating its switching mode, S1 or S2, which is used as control signal C for controlling the switching unit 33, the discriminator 32 is coupled to the radiation counter 34 (in switching mode S1 of the source 10) or to the scatter counter 35 (in switching mode S3 of the source 10).

The final counting signals of the radiation counter 34 and the scatter counter 35 at the end of the acquisition interval I are then provided to the scatter correction unit 18, where the scatter-corrected radiation signals are generated. This may be obtained in different ways.

Generally, there are readout time intervals and scatter time intervals with known durations. From the scatter data the cross-scatter rate can be derived by dividing the scatter counts by the integrated duration of the scatter readout. The radiation data contains known integral periods of scatter-free acquisitions plus contaminations by cross-scatter having an intensity that can be determined from the almost simultaneous (apart from small interleaving) scatter measurements. For instance, the following two ways of processing these data may be applied:

Subtract the expected contribution from cross-scatter included in the measurements (i.e. during acquisition mode A1 (for read-out unit 15) and A3 (for read-out unit 16), respectively) based on the measurement of the (pure) cross-scatter (i.e. during acquisition mode A2 (for read-out unit 15) and A4 (for read-out unit 16), respectively). This may be done by scaling the cross-scatter measurements (e.g. for detector 15 in acquisition mode A2) to the respective time durations (T3, T7, . . . ) and then using this scaled cross-scatter measurement to correct the other measurements (e.g. for detector 15 in acquisition mode A1), wherein the duration (T2, T4, . . . ) of the phases P2, in which both sources are switched on (and thus results in cross-scatter in the other measurements) is taken into account in this correction.

The acquired raw data are not corrected directly, but the information on the expected level of scatter is used in a maximum-likelihood estimate of the material decomposition. This option overcomes the first option's deficiency of ignoring the effects of the noise contribution of scatter. However, the first option can be implemented in a more straightforward manner.

In an alternative simple embodiment the switching unit 33 may be replaced by a logic using the control signal C (which may also be seen as an ON/OFF signal of source 10) to enable/disable the respective counter 34, 35 in opposite phases of the switching mode of the source 10.

In a still further embodiment a switching unit 10 is used to effect the counter selection, but in addition the above mentioned enabling logic for enabling/disabling the respective counter is used.

Generally, according to the present invention no limitations or constraints are made in terms of the duration of the ON and OFF phases of the different switching modes and acquisition modes. It is, however, generally assumed that the number of registered photons in the scatter counters is significantly lower than in the radiation counters.

The switch 33 mainly serves to make sure that corresponding counting data are always added up in the corresponding counters for the various phases. The detector cannot distinguish between a scatter photon and a signal photon.

Figure 4:
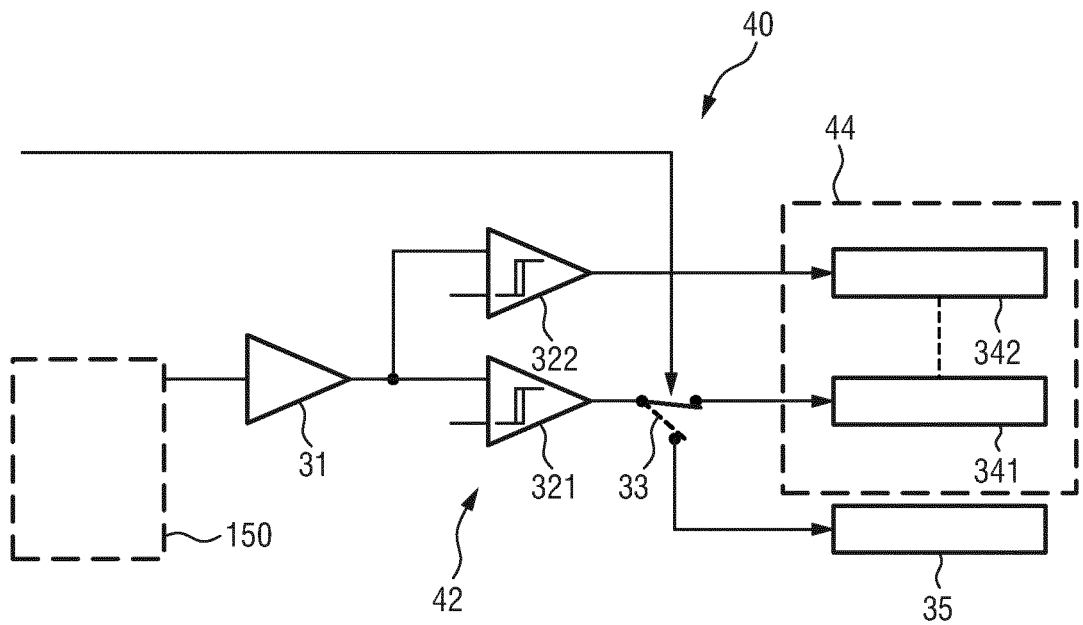
FIG. 4 shows a circuit diagram of a second embodiment of a read-out unit according to the present invention.

In the embodiment shown in FIG. 3 it was assumed that only one threshold is available. FIG. 4 shows a circuit diagram of a second embodiment of a read-out unit 40 according to the present invention applying a multi-bin topology. In this embodiment, the single radiation counter 34 is replaced by a multi-bin radiation counting unit 44 comprising multiple counters 341, 342, and the single discriminator 32 is replaced by a multi-bin discriminator unit 42 comprising multiple discriminators 321, 322 (applying different thresholds) coupled to the respective counter 341, 342 to obtain spectral information for the detected radiation.

In the read-out unit 40 a single scatter counter 35 at the lowest threshold is used, considering in this case that the energy information of the scatter photons is not of primary interest. In an alternative embodiment of a read-out unit 50 shown in FIG. 5 the same degree of spectral differentiation is provided for both primary and scattered photons. For this purpose the single scatter counter 35 is replaced by a multi-bin scatter counting unit comprising multiple counters 351, 352. Further, the single switch 33 is replaced by multiple switches 331, 332, which are all synchronously controlled by the control signal C.

Figure 5:
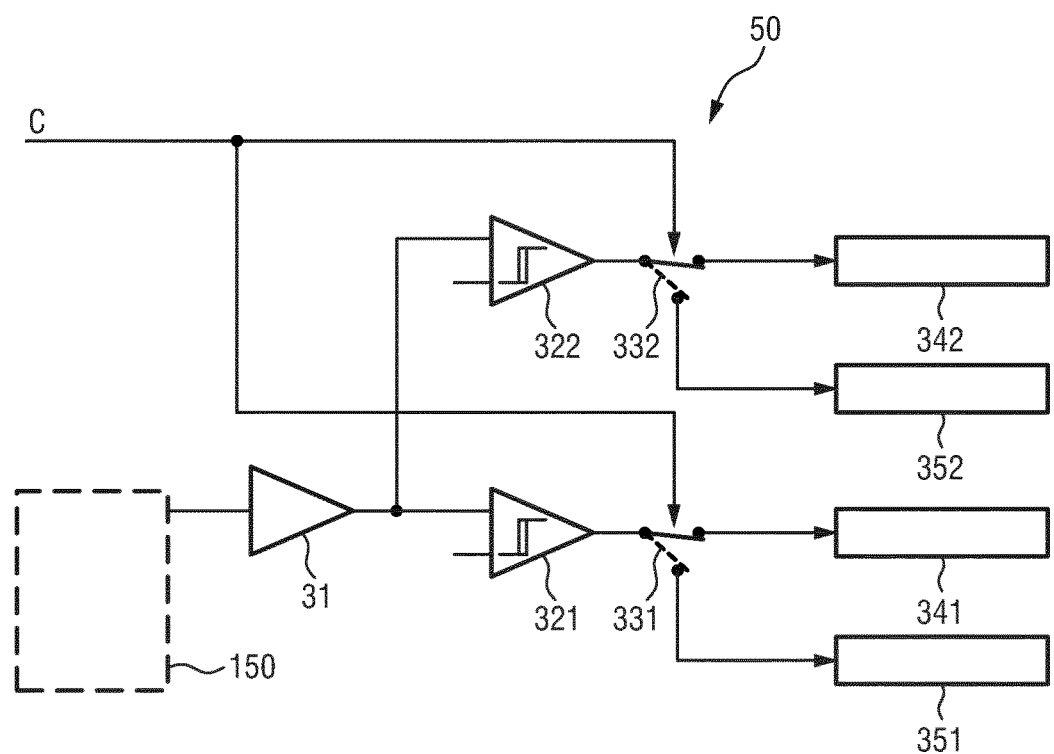
FIG. 5 shows a circuit diagram of a third embodiment of a read-out unit according to the present invention.
Figure 6:
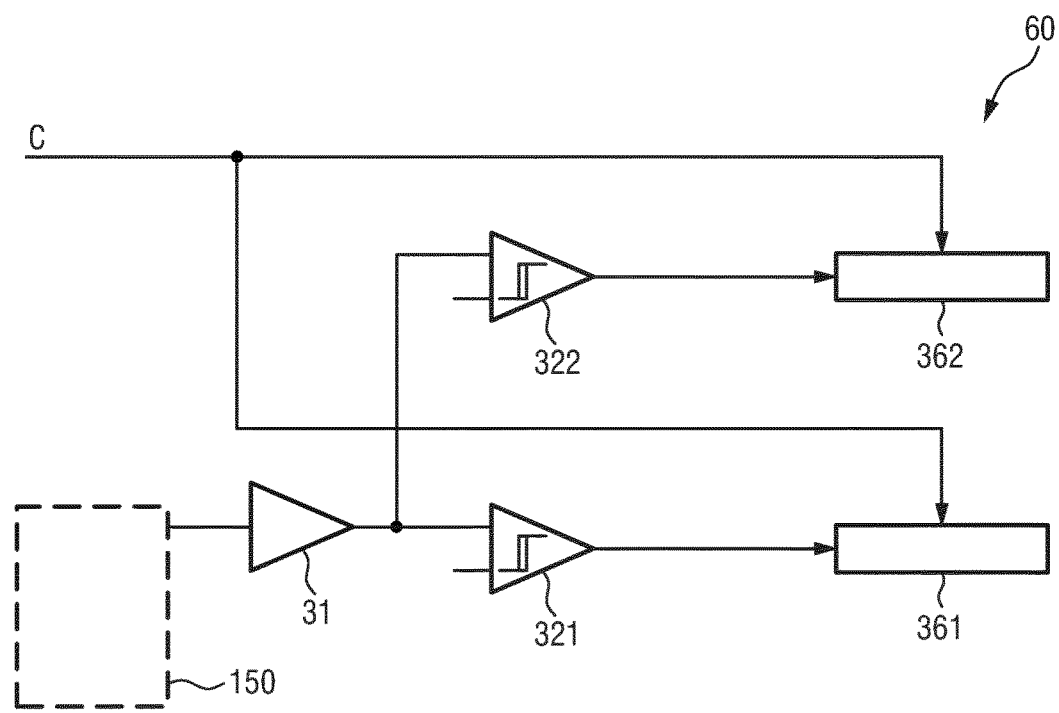
FIG. 6 shows a circuit diagram of a fourth embodiment of a read-out unit according to the present invention.

The embodiment shown in FIG. 5 requires using significantly more counters. Although the scatter counters 351, 352 are expected to require few bits, they may still require a non-negligible silicon area of the read-out unit 50. A possible way around this is to assume that the scatter events can simply be subtracted from the main events. On average this approximation is correct. FIG. 6 shows a circuit diagram of a corresponding embodiment of a read-out unit 60. As it can be seen, now only a set of counters 361, 362 is used (generally, a single counter may be sufficient if spectral information is not desired). However, the control signal C is not used to select one (or more) counter(s), e.g. by controlling a switch as shown in FIGS. 3 and 4, but to indicate whether a counter shall be incremented or decremented as follows: While e.g. source 10 is on, the counters 361, 362 coupled to its corresponding detector are allowed to increment upon registering counts (both direct and scattered). When the source 10 is switch off (and source 11 is switched on, i.e. in a phase P3), any registered event is subtracted from the same counters 361, 362. On average, the amount of events counted by the counters 361, 362 over the acquisition period I will correspond to a scatter-free acquisition.

This operation is valid as long as the ON and OFF phases (over a whole acquisition period I) have the same time duration. In case, the ON period is longer than the OFF period, this may be taken into consideration when decrementing the counters 361. For example, if the ON period is 5 times longer than the OFF period, the counters should be decremented 5 times for every single registered event during the OFF phase of the respective source. The idea here is to subtract in hardware from the radiation data one event per registered scatter event. For this to works the scatter time period included in the radiation data shall be equal to the duration of the scatter sampling. Otherwise rescaling may be needed.

In further embodiments the thresholds of the discriminator(s) may be made independent for both primary and cross-scattered photons. Further, the switch(es) may be arranged either before or after the discriminator(s).

In the embodiment illustrated by use of the timing diagram shown in FIG. 2 it was assumed that in the acquisition phases A1 and A3 of the respective read-out units 15, 16 photons are detected that impinge when both sources 10, 11 are active (in phases P2) as well when the opposite source is switched off (in phases P1 and P3). To some extent this operational mode may dilute the available information. Hence, in a further embodiment yet one other phase is considered as illustrated in the timing diagram shown in FIG. 7.

According to this embodiment each read-out unit 15, 16 has three distinct acquisition modes B1-B3 (for read-out unit 15) and B4-B6 (for read-out unit 16). Compared to the operation explained with reference to FIG. 2, the acquisition modes B1 (for the read-out unit 15) and B6 (for the read-out unit 16) have been added in which the respective read-out unit measures self-scatter. Phases P1 and P3 give estimates of the effects of scatter, but now for the read-out unit 15 the phase P1 (e.g. in time interval T1) is a cross-scatter-free phase and the phase P3 (e.g. in time interval T3) is a cross-scatter-only time interval, whereas for read-out unit 16 the phase P3 is a cross-scatter-free phase and the phase P1 is a cross-scatter-only time interval.

The cross-scatter correction of the mixed signal measurements (in acquisition mode B2 for read-out unit 15 and acquisition mode B5 for read-out unit 16, respectively) can be performed in the same way as explained above with respect to FIG. 2. The cross-scatter free signals measured in acquisition mode B1 for read-out unit 15 and acquisition mode B6 for read-out unit 16, respectively, need no correction, but these signals can be used together with the cross-scatter corrected signals for final signal estimation.

The OFF phases of the sources 10, 11 can be chosen very small, but should be long enough to provide sufficient photons yielding a good estimate of the involved scatter. For CT, typical readout durations (I in FIG. 2) range from 200-400 µs. Assuming a switching time of 1 µs (ON-OFF) one could think of sampling scatter for 10-40 µs with sampling transmission and scatter for 50-100 µs. Relative changes maybe 1:5 or 1:10 for scatter to radiation data.

In all the timing graphs it has been assumed that a projection (derived from the data in an acquisition interval) comprises a number of such acquisition phases (P1-P2-P3-P4). However, the present invention is not restricted to a specific sub-set or number of acquisition phases per acquisition interval. Furthermore, the phases or sub-intervals may or may not be synchronous with the acquisition time interval.

Figure 7:
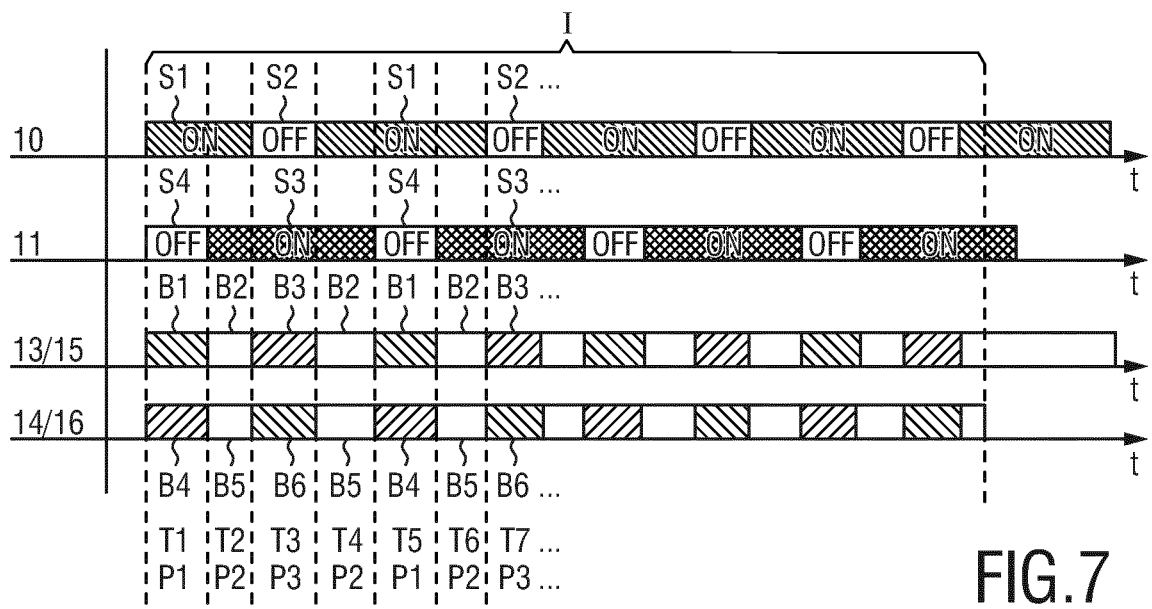
FIG. 7 shows a timing diagram illustrating a second implementation of the data acquisition.
Figure 8:
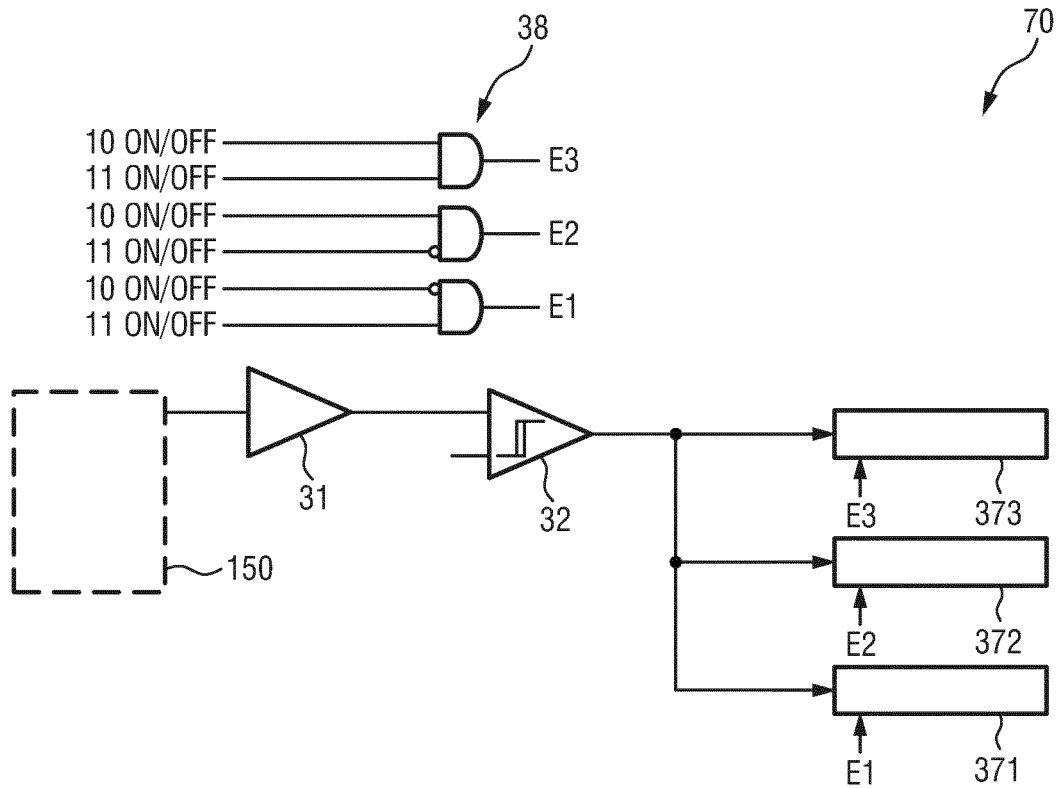
FIG. 8 shows a circuit diagram of a fifth embodiment of a read-out unit according to the present invention.

FIG. 8 shows a circuit diagram of a fifth embodiment of a read-out unit 70 according to the present invention for implementing the embodiment illustrated in FIG. 7. Based on the status of the sources 10, 11 three different enabling (control) signals E1, E2 and E3 are generated by an enabling logic 38 for enabling a respective counter 371, 372, 373. For read-out unit 15 the counter 371 is enabled during acquisition mode B3 (phase P3), the counter 372 is enabled during acquisition mode B1 (phase P1), and the counter 373 is enabled during acquisition mode B2 (phase P2). As for earlier embodiments, the radiation counters 371 and 372 are expected to be significantly smaller than the counter 373.

Figure 9:
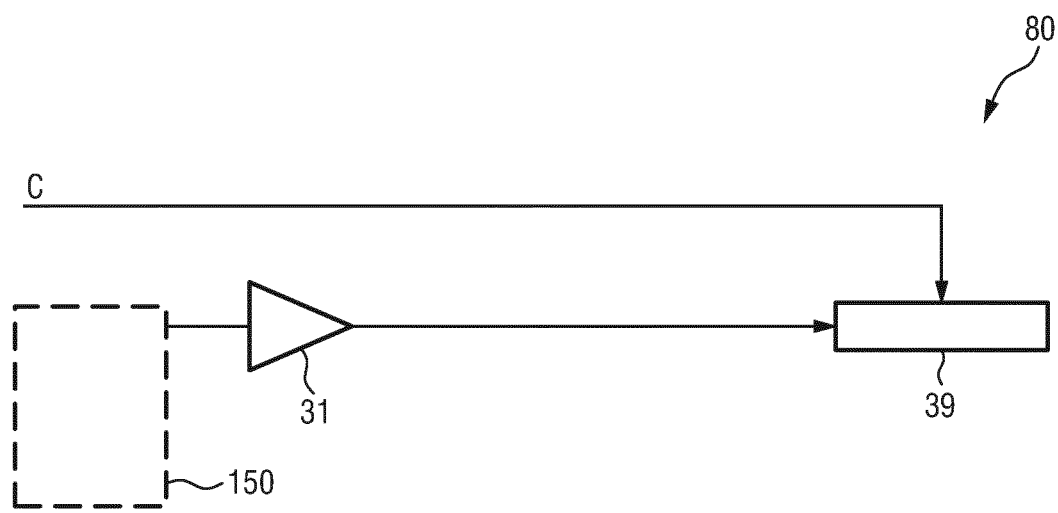
FIG. 9 shows a circuit diagram of a sixth embodiment of a read-out unit according to the present invention using integrators.
Figure 10:
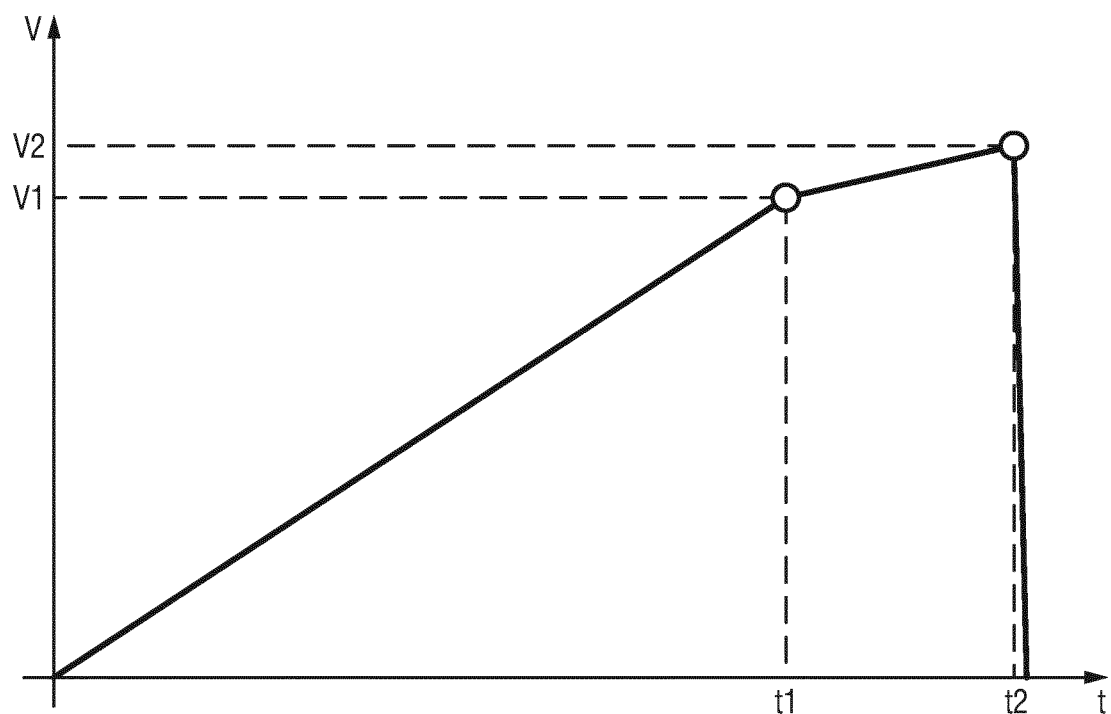
FIG. 10 shows a diagram explaining the use of integrators instead of counters.

In all the above embodiments, the use of photon counting detectors and read-out units was considered. The proposed dual-source CT system may, however, also use charge integrating type detectors and read-out units instead. Assuming the timing diagram shown in FIG. 2, a possible embodiment is depicted in FIG. 9 shows a circuit diagram of a sixth embodiment of a read-out unit 80 according to the present invention using an integrator 39. FIG. 10 shows a corresponding diagram explaining the use of integrators instead of counters. It shows particularly the integration signal V of the integrator 39 over time t.

In acquisition mode A1 (during time intervals T4, T5 and T6 for the read-out unit 15, as shown in FIG. 2), both primary and cross-scatter photons are integrated. At the end of said phase, at time t1 at the end of time interval T6, the value V1 of the integration signal V is sampled and transmitted for imaging purposes. In the subsequent acquisition mode A2 (during time interval T7) the corresponding source 10 is switched off, integrating therefore excess charge caused by cross-scattered photons from the other source 11. At the end of this phase, at time t2 at the end of time interval T7, the value V2 of the integration signal V is sampled. The difference between V2 and V1 gives the cross-scatter contribution, which can then be subtracted from the integration value V1 to obtain the scatter-corrected radiation signal.

In summary, the present invention provides an alternative and improved dual- (or multi-) source CT system and CT method, by which the negative effects of cross-scatter can be effectively suppressed or even completely eliminated. The invention can generally applied in any dual-source or multiple-source system with photon counting (pure counting or energy resolving) and/or integrating detectors and read-out units.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A CT system comprising:
   two x-ray sources for rotating about and concurrently or subsequently emitting radiation through an imaging region,
   two detectors, one per x-ray source, for detecting radiation after penetration through the imaging region,
   two read-out units, one per detector, for reading out the detected radiation from the respective detector,
   a control unit for controlling said x-ray sources by alternately switching each of said x-ray sources on and off so that in a first phase only the first x-ray source emits radiation, in a second phase both x-ray sources emit radiation and in a third phase only the second x-ray source emits radiation and for controlling said read-out units such that radiation detected by a detector during a phase in which the corresponding x-ray source is switched off is distinguished from radiation detected by the same detector during a phase in which the corresponding x-ray source is switched on, and
   a reconstruction unit for reconstructing a projection from a scatter-corrected readout-signal,
   wherein a scatter correction unit is provided or the read-out units are configured to generate scatter-corrected read-out signals from the detected radiation, wherein a scatter-corrected read-out signal is generated from the radiation detected by a detector during a single projection interval including multiple repetitions of said three phases and read out by the corresponding read-out unit.

2. The CT system as claimed in claim 1,
   wherein the read-out units are configured to take the time length of said three different phases into account in the generation of the scatter-corrected read-out signals.

3. The CT system as claimed in claim 1,
   wherein each read-out unit comprises a counter configured to increment its count based on radiation detected by the corresponding detector during phases in which the corresponding x-ray source is switched on and to decrement its count based on radiation detected by the corresponding detector during phases in which the corresponding x-ray source is switched off.

4. The CT system as claimed in claim 3,
   wherein the counters are configured to decrement its count based on radiation detected by the corresponding detector during phases in which the corresponding x-ray source is switched off multiplied by a correction factor corresponding to the ratio of the time length of the phases in which the corresponding x-ray source is switched on to the time length of the phases in which the corresponding x-ray source is switched off.

5. The CT system as claimed in claim 1,
   wherein each read-out unit comprising a scatter counter and a radiation counter,
   wherein the control unit is configured to control the read-out units such that radiation detected by a detector during a phase in which the corresponding x-ray source is switched off is read out by the scatter counter of the corresponding read-out unit to obtain a scatter signal and that radiation detected by the same detector during a phase in which the corresponding x-ray source is switched on is read out by the radiation counter of the same read-out unit to obtain a radiation signal, and
   wherein the read-out units are further configured to correct scatter by subtracting the scatter signal from the radiation signal read out by the scatter counter and the radiation counter of the same read-out unit to obtain the scatter-corrected read-out signals.

6. The CT system as claimed in claim 5,
   wherein each read-out unit comprises a switch controlled by the control unit to switch the detected radiation to scatter counter or the radiation counter in the respective phases.

7. The CT system as claimed in claim 5,
   wherein each read-out unit comprises an enabling logic controlled by the control unit to enable or disable the scatter counter or the radiation counter in the respective phases.

8. The CT system as claimed in claim 5,
   wherein each read-out unit comprises two or more radiation counters and/or two or more scatter counters for energy-dispersive counting.

9. The CT system as claimed in claim 1,
wherein the control unit is configured to control said read-out units such that radiation detected by a detector during the three different phases is distinguished and that a scatter-corrected read-out signal is generated by the read-out unit corresponding to said detector from the detected radiation in the three different phases.

10. The CT system as claimed in claim 1,
wherein each read-out unit comprises an integrator configured to provide an integration value after each phase, which are used for generating said scatter-corrected read-out signals.

11. The CT system as claimed in claim 1,
wherein the control unit is configured to control said scatter correction unit or said read-out units such that subsequent scatter-corrected read-out signals are each generated from the radiation detected by a detector during subsequent projection intervals each having the same duration.

12. The CT system as claimed in claim 1,
wherein the control unit is configured to control said x-ray sources to alternately switch each of said x-ray sources on and off according to the same switching pattern during subsequent projection intervals.

13. A CT method using a CT system comprising two x-ray sources for rotating about and concurrently or subsequently emitting radiation through an imaging region, two detectors, one per x-ray source, for detecting radiation after penetration through the imaging region, and two read-out units, one per detector, for reading out the detected radiation from the respective detector, said CT method comprising:
  controlling said x-ray sources by alternately switching each of said x-ray sources on and off so that in a first phase only the first x-ray source emits radiation, in a second phase both x-ray sources emit radiation and in a third phase only the second x-ray source emits radiation,
  controlling said read-out units such that radiation detected by a detector during a phase in which the corresponding x-ray source is switched off is distinguished from radiation detected by the same detector during a phase in which the corresponding x-ray source is switched on,
  generating scatter-corrected read-out signals from the detected radiation, wherein a scatter-corrected read-out signal is generated from the radiation detected by a detector during a single projection interval including multiple repetitions of said three phases and read out by the corresponding read-out unit, and
  reconstructing a projection from the scatter-corrected readout-signals.

14. A computer program comprising program code means for causing a computer to carry out the steps of the method as claimed in claim 13 when said computer program is carried out on the computer.

* * * * *